(12) United States Patent
Jaryal et al.

(10) Patent No.: US 8,552,197 B2
(45) Date of Patent: Oct. 8, 2013

(54) SORAFENIB ETHYLSULFONATE SALT, PROCESS FOR PREPARATION AND USE

(75) Inventors: Jagdev Singh Jaryal, Kangra (IN); Swargam Sathyanarayana, Karim Nagar (IN); Rajesh Kumar Thaper, Jammu (IN); Mohan Prasad, Gurgaon (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 13/508,878

(22) PCT Filed: Nov. 12, 2010

(86) PCT No.: PCT/IB2010/055151
§ 371 (c)(1),
(2), (4) Date: Jun. 22, 2012

(87) PCT Pub. No.: WO2011/058522
PCT Pub. Date: May 19, 2011

(65) Prior Publication Data
US 2013/0005777 A1    Jan. 3, 2013

(30) Foreign Application Priority Data
Nov. 12, 2009    (IN) .......................... 2335/DEL/2009

(51) Int. Cl.
*A61K 31/44*    (2006.01)
*C07D 211/72*    (2006.01)

(52) U.S. Cl.
USPC ....................................... 546/268.1; 514/350

(58) Field of Classification Search
None
See application file for complete search history.

(56) References Cited

U.S. PATENT DOCUMENTS

| | | | |
|---|---|---|---|
| 8,168,630 B2 | 5/2012 | Tamura et al. | 514/227.2 |
| 8,173,642 B2 | 5/2012 | Kobayashi et al. | 514/227.2 |
| 2010/0160290 A1 | 6/2010 | Kobayashi et al. | 514/211.01 |

FOREIGN PATENT DOCUMENTS

| | | |
|---|---|---|
| CN | 101 584 661 | 11/2009 |
| WO | WO 00/42012 | 7/2000 |
| WO | WO 2006/034796 | 4/2006 |
| WO | WO 2006/034797 | 4/2006 |
| WO | WO 2006034796 A1 * | 4/2006 |
| WO | WO 2007/049532 | 5/2007 |
| WO | WO 2007/068383 | 6/2007 |
| WO | WO 2007068383 A1 * | 6/2007 |
| WO | WO 2008/133273 | 11/2008 |
| WO | WO 2008/133274 | 11/2008 |
| WO | WO 2009/034308 | 3/2009 |
| WO | WO 2009/054004 | 4/2009 |
| WO | WO 2009/092070 | 7/2009 |
| WO | WO 2009/106825 | 9/2009 |

* cited by examiner

*Primary Examiner* — Janet Andres
*Assistant Examiner* — Heidi Reese

(57) ABSTRACT

The present invention provides sorafenib ethane sulphonate, process for its preparation, pharmaceutical composition comprising sorafenib ethane sulphonate and its use for the treatment of cancer. Formula (III).

Formula III

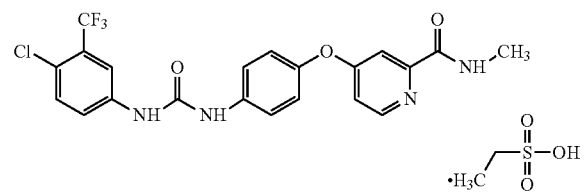

10 Claims, 4 Drawing Sheets

SORAFENIB ETHYLSULFONATE SALT, PROCESS FOR PREPARATION AND USE

FIELD OF THE INVENTION

The present invention provides for compositions of sorafenib ethane sulphonate, and a process for its preparation.

BACKGROUND OF THE INVENTION

Sorafenib is an inhibitor of the enzyme raf kinase known from WO 00/42012. It is chemically described as 4-(4-{3-[4-Chloro-3-(trifluoromethyl)phenyl]ureido}phenoxy)-$N^2$-methylpyridine-2-carboxamide, having a structure as represented by Formula I.

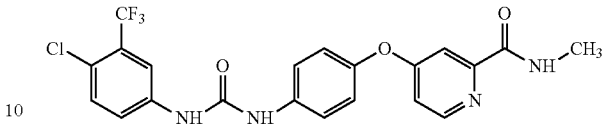

Formula I

Sorafenib is marketed in the United States as a tosylate salt as shown in Formula II under the brand name Nexavar®.

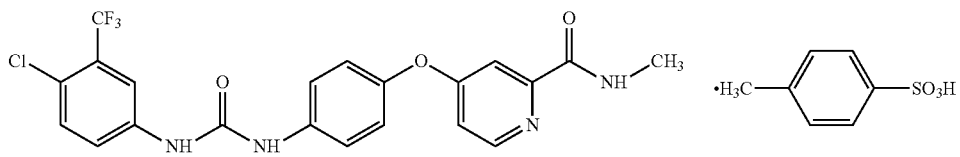

Formula II

Several acid addition salts of sorafenib are disclosed in WO 00/42012. Sorafenib ethane sulphonate salt of the present invention is not disclosed in the literature.

SUMMARY OF THE INVENTION

In one general aspect, the present invention provides for sorafenib ethane sulphonate of Formula III,

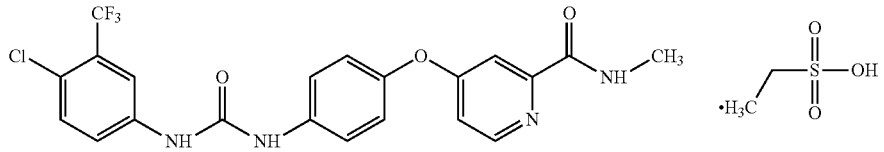

Formula III solvates, hydrates and polymorphs thereof.

Embodiments of this aspect may include one or more of the following features. For example, the sorafenib ethane sulphonate of Formula III may be characterized by X-ray diffraction peaks at d-spacing at about 10.84, 5.59, 5.22, 3.80, and 3.75 Å. The sorafenib ethane sulphonate of Formula III may be further characterized by X-ray diffraction peaks at d-spacing at about 5.41, 4.33, 3.47, 3.12, and 3.05 Å. The sorafenib ethane sulphonate of Formula III may also be characterized by a DSC thermogram having endotherm at about 208.10° C.

The sorafenib ethane sulphonate of Formula III may also be characterized by the X-ray diffraction pattern as depicted in FIG. 1, by the DSC as depicted in FIG. 2, the TGA as depicted in FIG. 3, and/or the IR spectrum as depicted in FIG. 4.

The sorafenib ethane sulphonate of Formula III may have a purity greater than 99% HPLC.

In another general aspect, the present invention provides for a process for the preparation of sorafenib ethane sulphonate of Formula III.

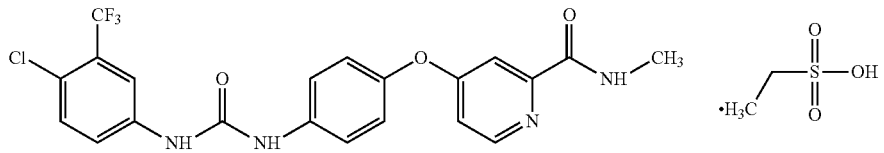

Formula III

The process includes contacting sorafenib free base of Formula I,

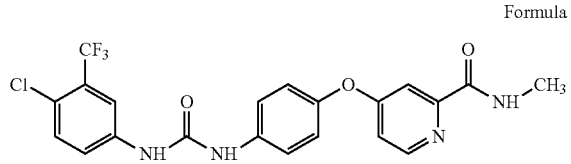

Formula I with ethane sulphonic acid.

Embodiments of this aspect may include one or more of the following features. For example, the process utilizes isolated sorafenib free base of Formula I or the sorafenib free base of Formula I, which is obtained as a solution directly from a reaction in which sorafenib free base is formed.

The sorafenib free base of Formula I is contacted with ethane sulphonic acid in a suitable solvent selected from water, polar organic solvents, dipolar aprotic organic solvents, and mixtures thereof. The polar organic solvent is selected from organic solvents containing at least one hydroxyl group, cyclic ethers, alkyl acetates and mixtures thereof. The organic solvent containing at least one hydroxyl group is selected from methanol, ethanol, n-propanol, isopropanol, n-butanol, sec-butanol, isobutanol, n-pentanol, glycerol or ethylene glycol. The dipolar aprotic organic solvent is selected from the group comprising of ketones, amides, nitriles, sulphoxides, or mixtures thereof.

The sorafenib free base is contacted with ethane sulphonic acid at about 0° C. to the reflux temperature of the suitable solvent.

In another general aspect, the present invention provides for the use of sorafenib ethane sulphonate of Formula III,

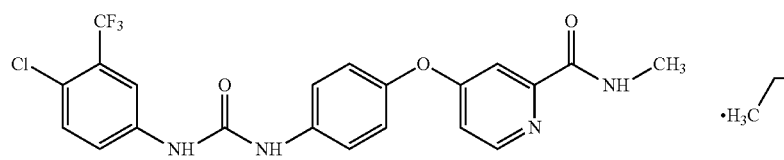

Formula III for the preparation of sorafenib acid addition salts of Formula IV.

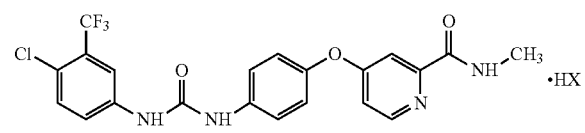

Formula IV

The process includes contacting sorafenib ethane sulphonate with an acid of Formula HX.

In yet another general aspect, the present invention provides for a pharmaceutical composition which includes sorafenib ethane sulphonate of Formula III and one or more pharmaceutically acceptable excipients.

DETAILED DESCRIPTION OF THE INVENTION

Figure 1:
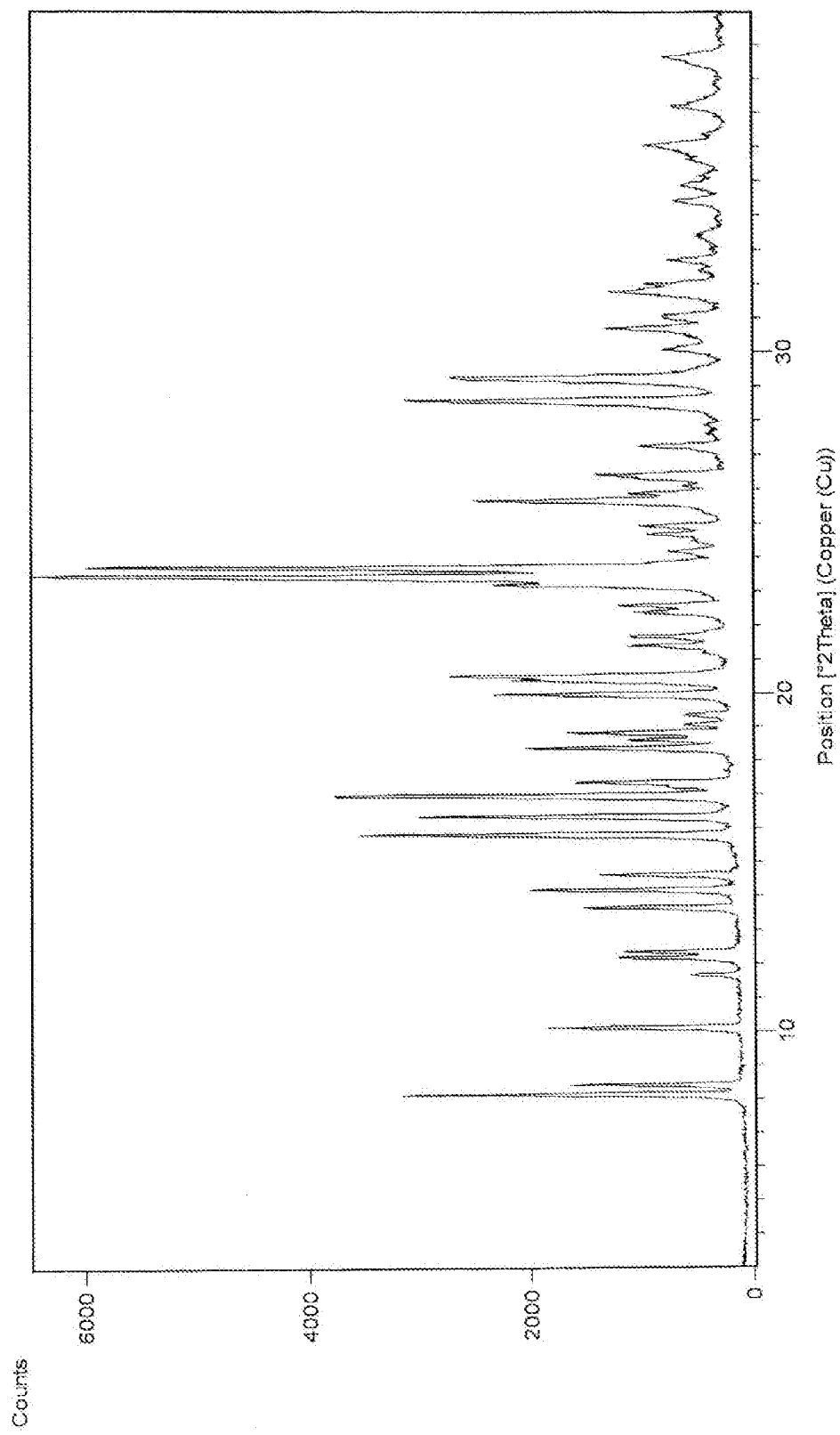
FIG. 1: X-ray Diffraction pattern (XRD) of sorafenib ethane sulphonate.

In one embodiment, the present invention provides for sorafenib ethane sulphonate of Formula III as characterized by XRD peaks at about 8.15 (d-spacing at 10.84 Å), 15.83 (5.59 Å), 16.97 (5.22 Å), 23.40 (3.80 Å), and 23.66 (3.75 Å)±0.2° 2θ.

In another embodiment, the present invention provides for sorafenib ethane sulphonate of Formula III as further characterized by XRD peaks at about 16.36 (5.41 Å), 20.49 (4.33 Å), 25.63 (3.47 Å), 28.56 (3.12 Å), and 29.23 (3.05 Å)±0.2° 2θ.

Sorafenib ethane sulphonate of Formula III may also be characterized by DSC thermogram having endotherms at about 208.10° C. It may also be characterized by XRD spectrum, DSC thermogram, TGA and IR spectra as depicted in FIGS. 1, 2, 3 and 4, respectively. Table 1 provides the d-spacing in Å and the corresponding 2θ values.

TABLE 1

| XRD Peaks of Sorafenib Ethane Sulphonate | | |
|---|---|---|
| Position (°2θ) | d-spacing (Å) | Relative Intensity (%) |
| 8.15 | 10.84 | 47.21 |
| 8.44 | 10.48 | 22.55 |
| 10.14 | 8.73 | 26.93 |
| 11.67 | 7.58 | 6.60 |

TABLE 1-continued

| XRD Peaks of Sorafenib Ethane Sulphonate | | |
|---|---|---|
| Position (°2θ) | d-spacing (Å) | Relative Intensity (%) |
| 12.19 | 7.26 | 17.22 |
| 12.37 | 7.15 | 15.67 |
| 13.67 | 6.48 | 21.66 |
| 14.20 | 6.24 | 29.39 |
| 14.64 | 6.05 | 19.95 |
| 15.83 | 5.59 | 53.63 |
| 16.36 | 5.41 | 44.79 |
| 16.97 | 5.22 | 56.44 |
| 17.37 | 5.11 | 22.84 |
| 18.38 | 4.83 | 29.38 |
| 18.63 | 4.76 | 15.21 |
| 18.84 | 4.71 | 24.12 |
| 19.09 | 4.65 | 6.80 |
| 19.35 | 4.59 | 7.08 |
| 19.96 | 4.45 | 33.92 |
| 20.35 | 4.36 | 29.92 |
| 20.49 | 4.33 | 39.85 |
| 21.38 | 4.15 | 14.45 |
| 21.65 | 4.11 | 14.47 |

TABLE 1-continued

XRD Peaks of Sorafenib Ethane Sulphonate

| Position (°2θ) | d-spacing (Å) | Relative Intensity (%) |
|---|---|---|
| 22.35 | 3.98 | 13.36 |
| 22.56 | 3.94 | 16.01 |
| 23.15 | 3.84 | 31.98 |
| 23.40 | 3.80 | 100.00 |
| 23.66 | 3.75 | 92.08 |
| 24.14 | 3.69 | 8.49 |
| 24.66 | 3.61 | 11.56 |
| 24.89 | 3.58 | 12.41 |
| 25.63 | 3.47 | 36.67 |
| 25.85 | 3.45 | 14.31 |
| 26.39 | 3.38 | 18.65 |
| 27.23 | 3.27 | 11.94 |
| 28.56 | 3.12 | 45.78 |
| 29.23 | 3.05 | 38.90 |
| 30.05 | 2.97 | 8.51 |
| 30.69 | 2.91 | 17.11 |
| 31.05 | 2.88 | 8.92 |
| 31.74 | 2.82 | 15.05 |
| 31.98 | 2.80 | 11.18 |
| 32.71 | 2.74 | 7.77 |
| 33.44 | 2.68 | 3.54 |
| 34.40 | 2.61 | 6.71 |
| 34.87 | 2.57 | 5.85 |
| 36.07 | 2.49 | 10.18 |
| 37.19 | 2.42 | 7.02 |
| 38.64 | 2.33 | 7.74 |

The sorafenib free base of Formula I which is used for the preparation of sorafenib ethane sulphonate of Formula III, may be obtained by any of the methods known in the literature, such as those described in PCT applications WO 00/42012; WO 2006/034796; WO 2006/034797; WO 2009/034308; WO 2009/054004; WO 2009/106825; and WO 2009/092070, which are herein incorporated by reference.

In general, the sorafenib free base of Formula I may be prepared by the reaction of 4-(2-(N-methylcarbamoyl)-4-pyridyloxy)aniline with 4-chloro-3-(trifluoromethyl)phenyl isocyanate. The starting sorafenib free base of Formula I may be obtained as a solution directly from a reaction in which sorafenib free base is formed and used as such without isolation.

The term "contacting" may include dissolving, slurrying, stirring, or a combination thereof.

The reaction of the sorafenib free base of Formula I with ethane sulphonic acid may be carried out by directly contacting sorafenib free base with ethane sulphonic acid. The reaction may also be carried out in the presence of a suitable solvent. A solution of ethane sulphonic acid in a suitable solvent may also be used. Preferably, ethane sulphonic acid may be added to a reaction mixture containing sorafenib free base and a suitable solvent.

The suitable solvent may be selected from water, polar organic solvents, dipolar aprotic organic solvents, and mixtures thereof.

The polar organic solvents may be selected from organic solvents containing at least one hydroxyl group, cyclic ethers, alkyl acetates, and mixtures thereof. Examples of organic solvents containing at least one hydroxyl group may include methanol, ethanol, n-propanol, isopropanol, n-butanol, sec-butanol, isobutanol, n-pentanol, glycerol or ethylene glycol. Examples of cyclic ethers may include tetrahydrofuran or 1,4-dioxane. Examples of alkyl acetates may include methyl acetate, ethyl acetate, propyl acetate, or butyl acetate.

The dipolar aprotic organic solvents may be selected from the group comprising of ketones, amides, nitriles, sulphoxides, or mixtures thereof. Examples of ketones may include acetone, methyl ethyl ketone, or methyl isobutyl ketone. Examples of amides may include N,N-dimethylformamide, or N,N-dimethylacetamide. Examples of nitriles may include acetonitrile, or propionitrile. Examples of sulphoxides may include dimethyl sulfoxide, or diethyl sulphoxide.

In the preferred embodiments of the present invention, the reaction of sorafenib free base with ethane sulphonic acid may be carried out in polar organic solvents selected from organic solvents containing at least one hydroxyl group, such as methanol, ethanol, n-propanol, isopropanol, n-butanol, sec-butanol, isobutanol, n-pentanol, glycerol, or ethylene glycol.

Ethane sulphonic acid may be added slowly to the reaction mixture containing sorafenib free base and the suitable solvent.

In the preferred embodiment of the present invention ethane sulphonic acid may be added to the reaction mixture containing sorafenib free base and the suitable solvent over a period of about 20 minutes, preferably, about 10 minutes.

The reaction of sorafenib free base with ethane sulphonic acid may be carried out at a temperature of about 0° C. to the reflux temperature of the suitable solvent, preferably, at about 15° C. to about 80° C., most preferably, at about 15° C. to about 35° C.

The solution may be stirred for about 30 minutes to about 8 hours, preferably, for about 4 hours.

The reaction mixture containing sorafenib free base, ethane sulphonic acid and solvent(s) may be treated with a decolorizing agent such as activated charcoal before precipitation.

Generally, an ethane sulphonate salt of sorafenib precipitates out of the reaction mixture. The precipitation may be spontaneous depending upon the solvent used and the reaction conditions. The precipitation may also be facilitated by seeding or by reducing the temperature.

Isolation of the ethane sulphonate salt of sorafenib may be accomplished by concentration, precipitation, cooling, filtration or centrifugation, or a combination thereof, followed by drying under reduced pressure. The sorafenib ethane sulphonate may be further purified by recrystallization for better purity.

The process of the present invention provides sorafenib ethane sulphonate of high purity.

The sorafenib ethane sulphonate of Formula III may be converted into a sorafenib free base of Formula I of high purity by hydrolysis in a neutral medium or in the presence of a base. The base may be selected from hydroxides, carbonates and bicarbonates of alkali and alkaline earth metals, ammonia, alkyl amines, hydrazine, and the like. Examples of hydroxides, carbonates and bicarbonates of alkali and alkaline earth metals may include lithium hydroxide, sodium hydroxide, potassium hydroxide, sodium carbonate, potassium carbonate, sodium bicarbonate or potassium bicarbonate. Examples of alkyl amines may include diethyl amine, triethyl amine or methyl diethyl amine.

The processes of the present invention provides sorafenib free base of high purity.

The conversion of the sorafenib ethane sulphonate of Formula III to sorafenib acid addition salts of Formula IV may be carried out by directly contacting sorafenib with an acid of Formula HX.

The acid of Formula HX may be selected from the group comprising hydrochloric acid, hydrobromic acid, sulfuric acid, phosphoric acid, methanesulphonic acid, trifluoromethanesulfonic acid, benzenesulfonic acid, para-toluene sulphonic acid, 1-naphthalenesulfonic acid, 2-naphthalenesulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid or mandelic acid.

The conversion of the sorafenib ethane sulphonate of Formula III to the sorafenib acid addition salts of Formula IV may also be carried out by a process comprising conversion of sorafenib ethane sulphonate to sorafenib free base in the first step followed by the reaction of sorafenib free base with the acid of Formula HX.

In a preferred embodiment of the present invention, sorafenib ethane sulphonate may be converted to sorafenib tosylate by heating a reaction mixture containing sorafenib ethane sulphonate, ethyl acetate and water to a temperature of about 70° C.; slowly adding a solution of para-toluene sulphonic acid monohydrate in ethyl acetate-water mixture to the above reaction mixture over a period of about 30 minutes; cooling the reaction mixture to about 32° C.; stiffing overnight; further cooling to about 0° C. to about 5° C.; and stirring for about 3 hours. Sorafenib tosylate may be obtained from the above reaction mixture by slowly raising the temperature to about 32° C., and filtering and drying under reduced pressure. Drying may be carried out at about 55° C. for about 5 hours.

Solvates, hydrates and polymorphs of sorafenib ethane sulphonate of Formula III are also included within the scope of the present invention. Polymorphs of sorafenib ethane sulphonate may include both amorphous and crystalline forms.

The amorphous form may be obtained by conventional methods such as spray drying, lyophilization and evaporation of the solvent under reduced pressure.

Sorafenib ethane sulphonate is usually administered as part of a pharmaceutical composition. Accordingly, in a further aspect, there is provided a pharmaceutical composition that comprises ethane sulphonate salt of sorafenib and one or more pharmaceutically acceptable carriers, diluents or excipients and optionally other therapeutic ingredients. Pharmaceutical compositions comprising the sorafenib ethane sulphonate of Formula III may be administered orally, topically, parenterally, by inhalation or spray, rectally or in the form of injectables. Injectables include intravenous, intramuscular, subcutaneous and parenteral injections, as well as use of infusion techniques.

In the foregoing section, embodiments are described by way of examples to illustrate the processes of invention. However, these are not intended in any way to limit the scope of the present invention. Several variants of the examples would be evident to persons ordinarily skilled in the art, which are within the scope of the present invention.

Methods

The XRD pattern was recorded using Panalytical Expert PRO with Xcelerator as detector, 3-40 as scan range, 0.02 as step size and 3-40° 2θ as range.

DSC and TGA were recorded using Mettler Toledo DSC 821e and TA instrument-Q 500, respectively.

HPLC was performed using a Zorbax SB AQ, 250 mm×4.6 mm, 5 μm column having the following parameters:

Flow rate: 1.0 mL/minute
Detector: UV at 260 nm
Injection volume: 10 μL
Column oven Temperature: 30° C.
Run time: 50 minutes
Buffer: Orthophosphoric acid in water
Mobile Phase: Buffer and Methanol

EXAMPLES

Example 1

Preparation of Sorafenib Ethane Sulphonate

Ethanol (20 mL) was added to a reaction vessel containing sorafenib free base (4.0 g). Ethane sulphonic acid (1.62 mL) was added drop wise to the above reaction mixture. The reaction mixture was stirred at about 25° C. to 35° C. for about 4 hours. The solid was filtered, washed with ethanol (2×10 mL) and dried under reduced pressure at about 60° C. for about 5 hours to obtain sorafenib ethane sulphonate.

Yield: 91%
HPLC Purity: 99.46%

Example 2

Preparation of Sorafenib Tosylate

A reaction mixture containing sorafenib ethane sulphonate (5.0 g), ethyl acetate (50 mL) and water (1 mL) was heated to about 70° C. A solution of para-toluene sulphonic acid monohydrate (3.3 g) in ethyl acetate: water:: 1.0 mL: 0.2 mL was slowly added over a period of about 30 minutes to the above reaction mixture. The reaction mixture was cooled to about 32° C. and stirred overnight. The reaction mixture was further cooled to about 0° C. to about 5° C. and stirred for about 3 hours. Temperature of the reaction mixture was slowly raised to about 32° C. The solid material was filtered and dried under reduced pressure at about 55° C. for about 5 hours to obtain sorafenib tosylate.

Yield: 36.1%

We claim:

1. Crystalline sorafenib ethane sulphonate of Formula III

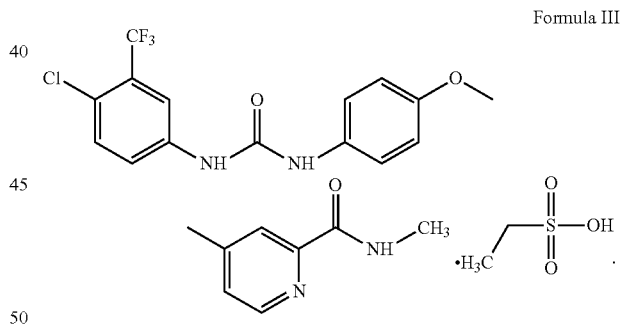

2. The crystalline sorafenib ethane sulphonate of claim 1, characterized by X-ray diffraction peaks comprising d-spacings at about 10.84, 5.59, 5.22, 3.80, and 3.75 Å.

3. The crystalline sorafenib ethane sulphonate of claim 1, further characterized by X-ray diffraction peaks comprising d-spacings at about 5.41, 4.33, 3.47, 3.12, and 3.05 Å.

4. The crystalline sorafenib ethane sulphonate of claim 1, characterized by a DSC thermogram having an endotherm at about 208.10° C.

5. The crystalline sorafenib ethane sulphonate of claim 1, characterized by the X-ray diffraction pattern as depicted in FIG. 1.

Figure 2:
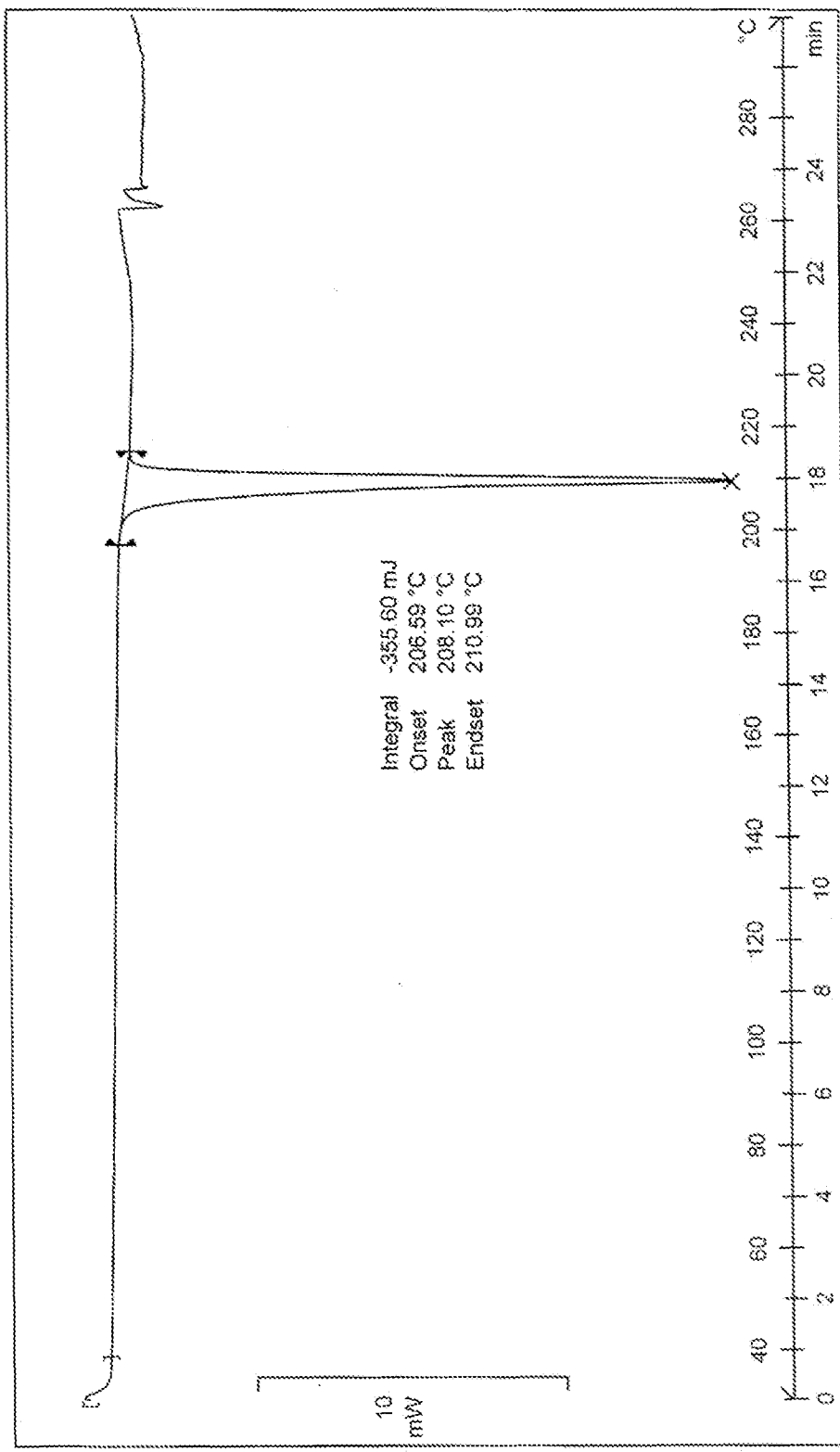
FIG. 2: Differential Scanning Thermogram (DSC) of sorafenib ethane sulphonate.

6. The crystalline sorafenib ethane sulphonate of claim 1, characterized by a DSC as depicted in FIG. 2.

Figure 3:
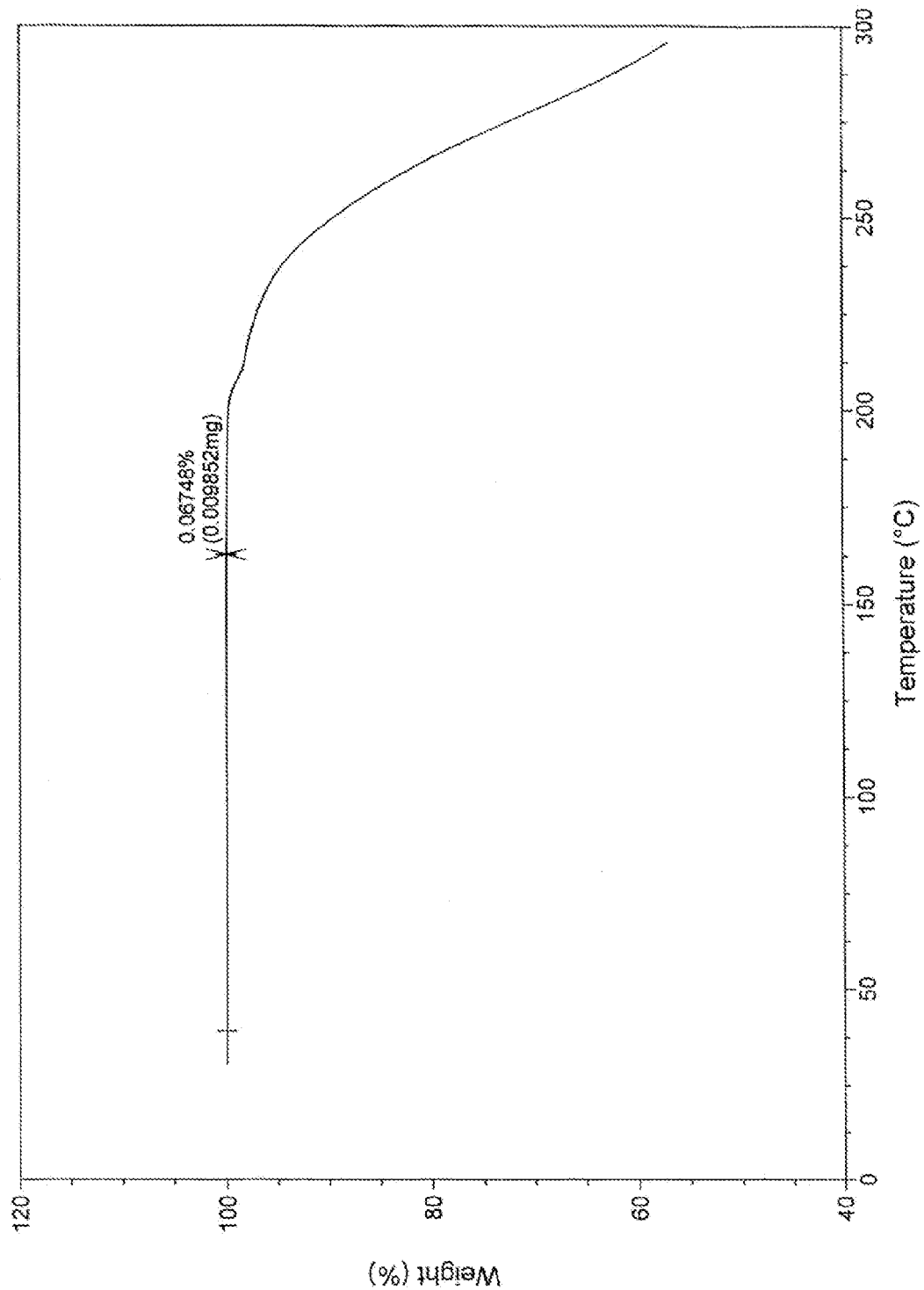
FIG. 3: Thermo Gravimetric analysis (TGA) of sorafenib ethane sulphonate.

7. The crystalline sorafenib ethane sulphonate of claim 1, characterized by a TGA as depicted in FIG. 3.

Figure 4:
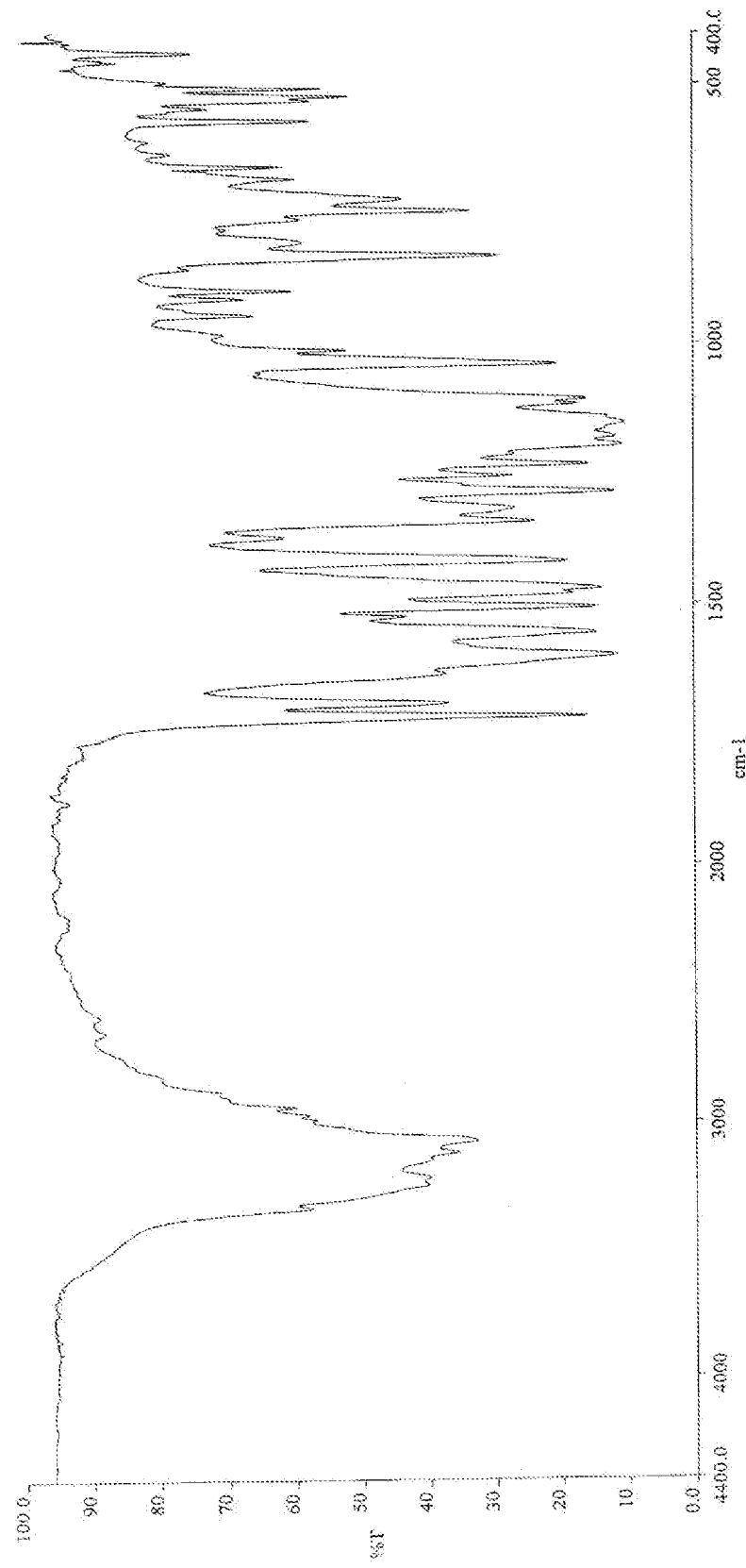
FIG. 4: Infra Red Spectrum (IR) of sorafenib ethane sulphonate.

8. The crystalline sorafenib ethane sulphonate of claim 1, characterized by an IR spectrum as depicted in FIG. 4.

9. The crystalline sorafenib ethane sulphonate of claim 1, having greater than 99% HPLC purity.

10. A pharmaceutical composition comprising crystalline sorafenib ethane sulphonate of Formula III, and one or more pharmaceutically acceptable excipients.

* * * * *

UNITED STATES PATENT AND TRADEMARK OFFICE
CERTIFICATE OF CORRECTION

| | | |
|---|---|---|
| PATENT NO. | : 8,552,197 B2 | Page 1 of 1 |
| APPLICATION NO. | : 13/508878 | |
| DATED | : October 8, 2013 | |
| INVENTOR(S) | : Jagdev Singh Jaryal | |

It is certified that error appears in the above-identified patent and that said Letters Patent is hereby corrected as shown below:

In the Specification:

Column 7, line 17:

"stiffing" should read --stirring--

Signed and Sealed this
Seventeenth Day of December, 2013

Margaret A. Focarino
*Commissioner for Patents of the United States Patent and Trademark Office*